US006648825B1

(12) United States Patent
Mesaros et al.

(10) Patent No.: US 6,648,825 B1
(45) Date of Patent: Nov. 18, 2003

(54) DIAGNOSTIC ULTRASOUND SYSTEM CART WITH SWIVELING CONTROL PANEL

(75) Inventors: Robert Mesaros, Bothell, WA (US); Yas Matsui, Redmond, WA (US); Jay Wilkins, Belgrade, MT (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/155,529

(22) Filed: May 23, 2002

(51) Int. Cl.[7] .................................................. A61B 8/00
(52) U.S. Cl. ....................................................... 600/437
(58) Field of Search ................................... 600/437–472

(56) References Cited

U.S. PATENT DOCUMENTS

| | | | | |
|---|---|---|---|---|
| 4,659,048 A | * | 4/1987 | Fahrion | 248/285.1 |
| 4,870,954 A | | 10/1989 | Satoh | |
| 5,129,397 A | * | 7/1992 | Jingu et al. | 600/437 |
| D360,690 S | * | 7/1995 | Murakami | D24/160 |
| D368,521 S | * | 4/1996 | Asai et al. | D24/160 |
| 5,924,988 A | * | 7/1999 | Burris et al. | 600/437 |
| 6,073,942 A | * | 6/2000 | Heneveld, Sr. | 280/33.991 |
| 6,215,846 B1 | * | 4/2001 | Mazess et al. | 378/62 |
| 6,315,445 B1 | * | 11/2001 | Mazess et al. | 378/196 |

* cited by examiner

*Primary Examiner*—Marvin M. Lateef
*Assistant Examiner*—William C. Jung
(74) *Attorney, Agent, or Firm*—W. Brinton Yorks, Jr.

(57) ABSTRACT

The control panel of an ultrasound system can swivel about the operator location. In one embodiment this capability is provided by pivoting the control panel about a pivot axis located forward of the center of the control panel, preferably within a few inches of the operator position. In another embodiment the control panel can be moved along a track which is curved about the operator position, and in a further embodiment the control panel is moved by a linkage which simultaneously moves the control panel from side to side and forward.

13 Claims, 14 Drawing Sheets

DIAGNOSTIC ULTRASOUND SYSTEM CART WITH SWIVELING CONTROL PANEL

This invention relates to ultrasonic diagnostic imaging systems and, in particular, to ultrasound systems with control panels that adjustably swivel.

Cart-borne ultrasound systems are convenient to use in a hospital, as they can be used in a dedicated imaging lab where they are essentially stationary, or can be rolled to a patient's bedside when a medical condition or other expedient dictates. Frequently there is not much room to manipulate the cart in a patient room or at a bedside, which can present an awkward or uncomfortable scanning situation for the system operator. For that reason among others ultrasound system control panels have been designed to pivot or swing from side to side, so that the operator can adjust the control panel to a comfortable operating and scanning position.

However the range or type of adjustment which can be made to the control panel's position may be other than that which is needed for operator comfort. Often the control panel will pivot or swing around the system cart as a pivot point, or will pivot about its own center. It has been found to be preferable for the operator to move the control panel around the operator's position. Once the operator is located where he or she can comfortably scan the patient, it is desirable that the control panel be able to pivot or swing about the operator's most comfortable scanning position.

In accordance with the principles of the present invention, an ultrasound system cart is provided with a control panel that swivels about the system operator. In one embodiment this motion is provided by an axis of rotation which is located in the forward half of the control panel which is closest to the operator. In another embodiment this motion is provided by movably mounting the control panel on a curved path which curves around the operator position. In a further embodiment this motion is provided by an articulating mechanism which enables the control panel to be moved around the operator position. Preferably the range of motion has detent positions and the control panel can be locked in its center position for travel.

Figure 1:
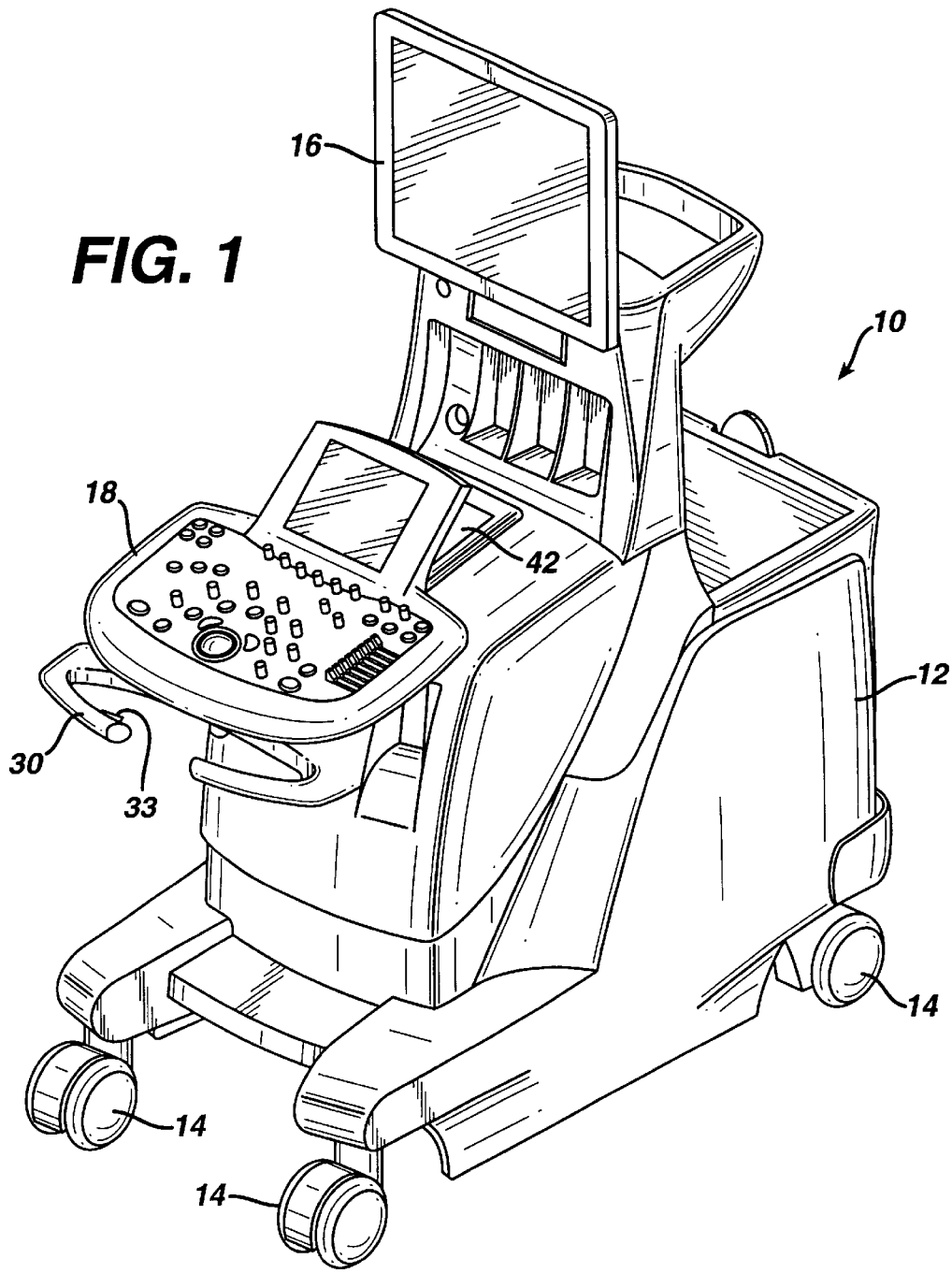
FIG. 1 illustrates a cart-borne ultrasound system in perspective.

Referring first to FIG. 1, a cart-borne ultrasound system 10 is shown in perspective. The cart includes an electronics bay 12 inside of which are located printed circuit boards for electronically processing received ultrasound signals. The ultrasound signals are processed to produce an image which is displayed on a display 16, the plane of which is aligned with an approximate laterally extending center line of the cart. The cart is mounted on wheels or casters 14 so that it can be rolled to a lab or a patient's bedside. In the front of the cart is a control panel 18 which contains a number of knobs, buttons, slide switches, and a trackball by which a user operates the ultrasound system. The control panel is mounted above a handle 30 which extends from the front of the ultrasound system. The handle 30 can be used to pull the cart to move it from one location to another. On the inside of the handle 30 is a handle lock release 33.

Figure 2:
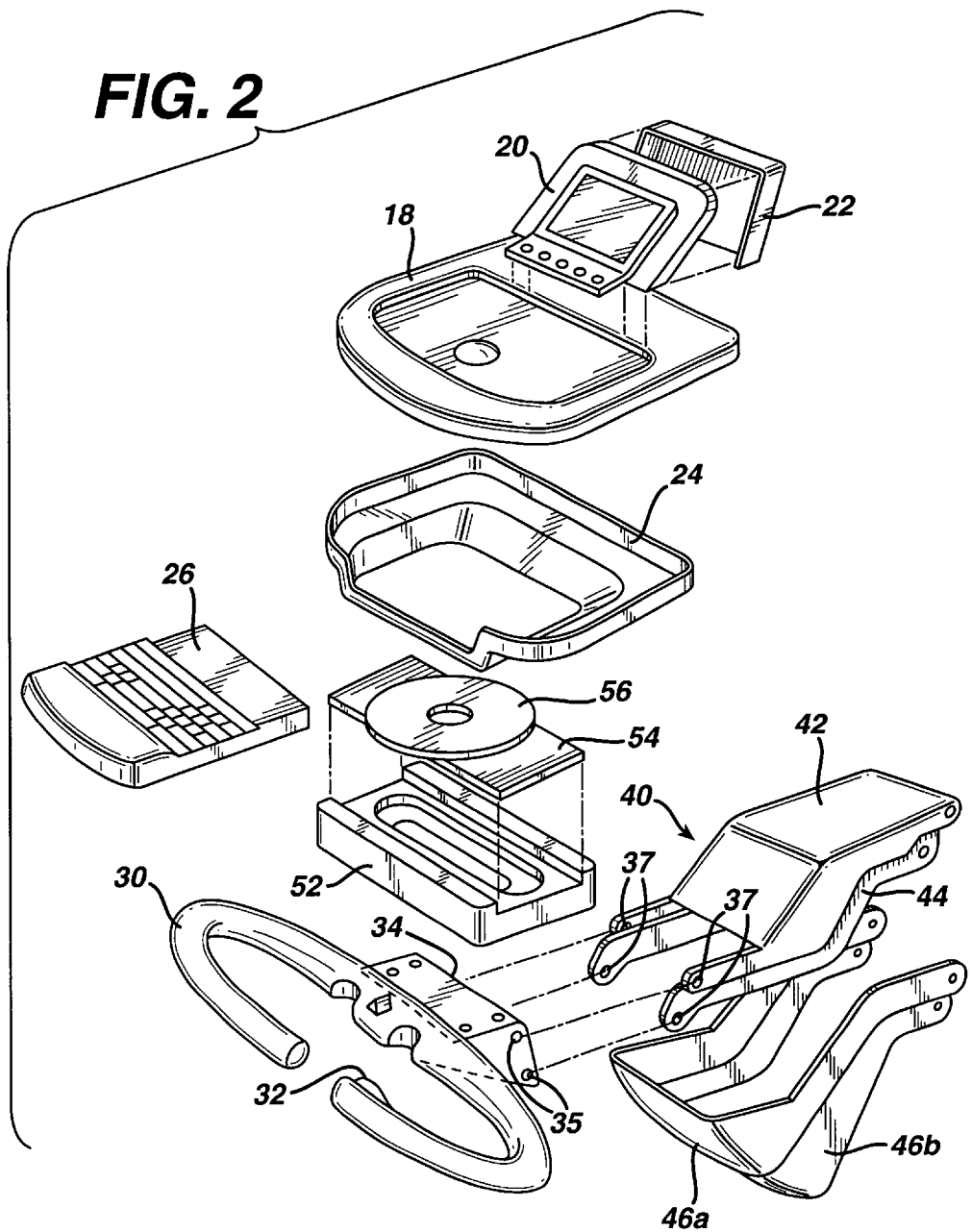
FIG. 2 is an exploded view of a control panel articulation assembly in accordance with a first embodiment of the present invention.

FIG. 2 is an exploded view of a control panel articulation assembly in accordance with a first embodiment of the present invention. The control panel 18 is mounted on a lift mechanism 40 which serves to elevate and lower the control panel to a height which is comfortable for the user. The lift mechanism 40 is more fully described in concurrently filed U.S. patent application Ser. No. 10/154,733, filed May 23, 2002. As described therein, the lift mechanism 40 includes a pivotally mounted lift top 42 and lift bottom 44 which are mounted to the ultrasound system cart at the rear of the mechanism. The lift mechanism 40 also includes lift assembly beard covers 46a and 46b, which prevent the appearance of pinch points beneath the lift top and bottom when the control panel is in an elevated position. When the user depresses a lift release 32 in the handle, the lift mechanism moves freely to raise and lower the control panel. When the lift release 32 is released, the lift mechanism locks in its current position.

The control panel includes a touchscreen 20 and touchscreen rear cover 22 which are mounted on the control panel 18. Below the control panel is a control panel bottom 24. A keyboard 26 can slide into and out of the compartment in the control panel bottom. The control panel bottom is mounted on a swivel plate 56 which rotates about a central pivot point. The swivel plate 56 is mounted on a lateral carriage 54. The lateral carriage can be moved laterally in the mating opening of a lateral track 52. The lateral track 52 is mounted on the top of a connection block 34, to which the handle 30 is also connected. The connection block 34 is movably mounted to the lift mechanism 40 through holes 35 and 37.

Figure 3:
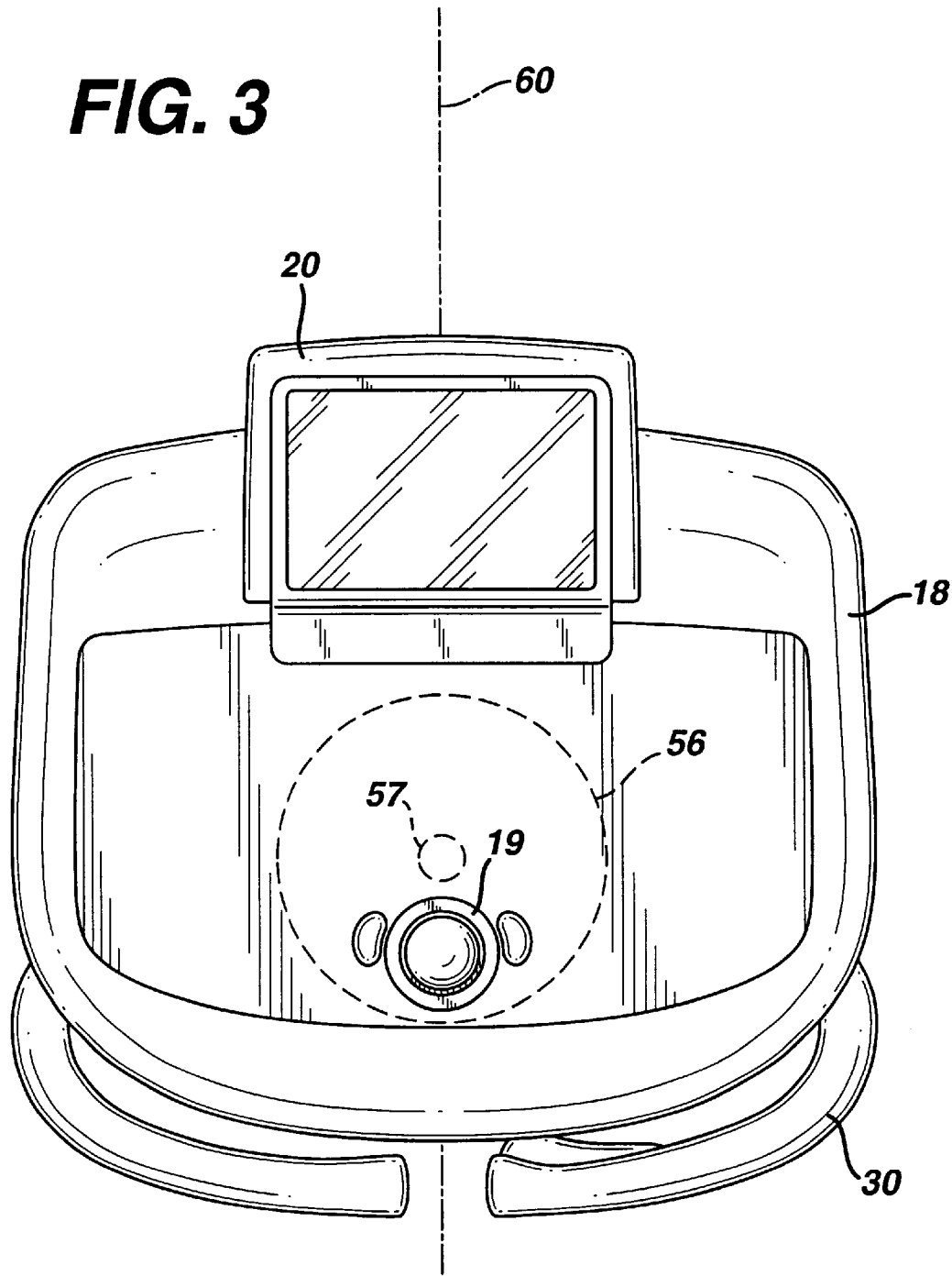
FIGS. 3–8 illustrate the range of control panel articulation provided by the first embodiment.

FIGS. 3–8 illustrate the range of control panel motion provided by the swivel plate 56, the lateral carriage 54, and the lateral track 52 of FIG. 2. In FIG. 3 the control panel 18 is shown in its nominal center (home) position as it appears in FIG. 1. The control panel can be locked firmly in this position. In this position the control panel is centered on a center axis 60, which will generally be aligned with the center of the ultrasound system cart as shown in FIG. 1. The swivel plate 56 and its central pivot point 57 are shown in phantom on the control panel 18, just behind the location of the trackball 19.

Figure 4:
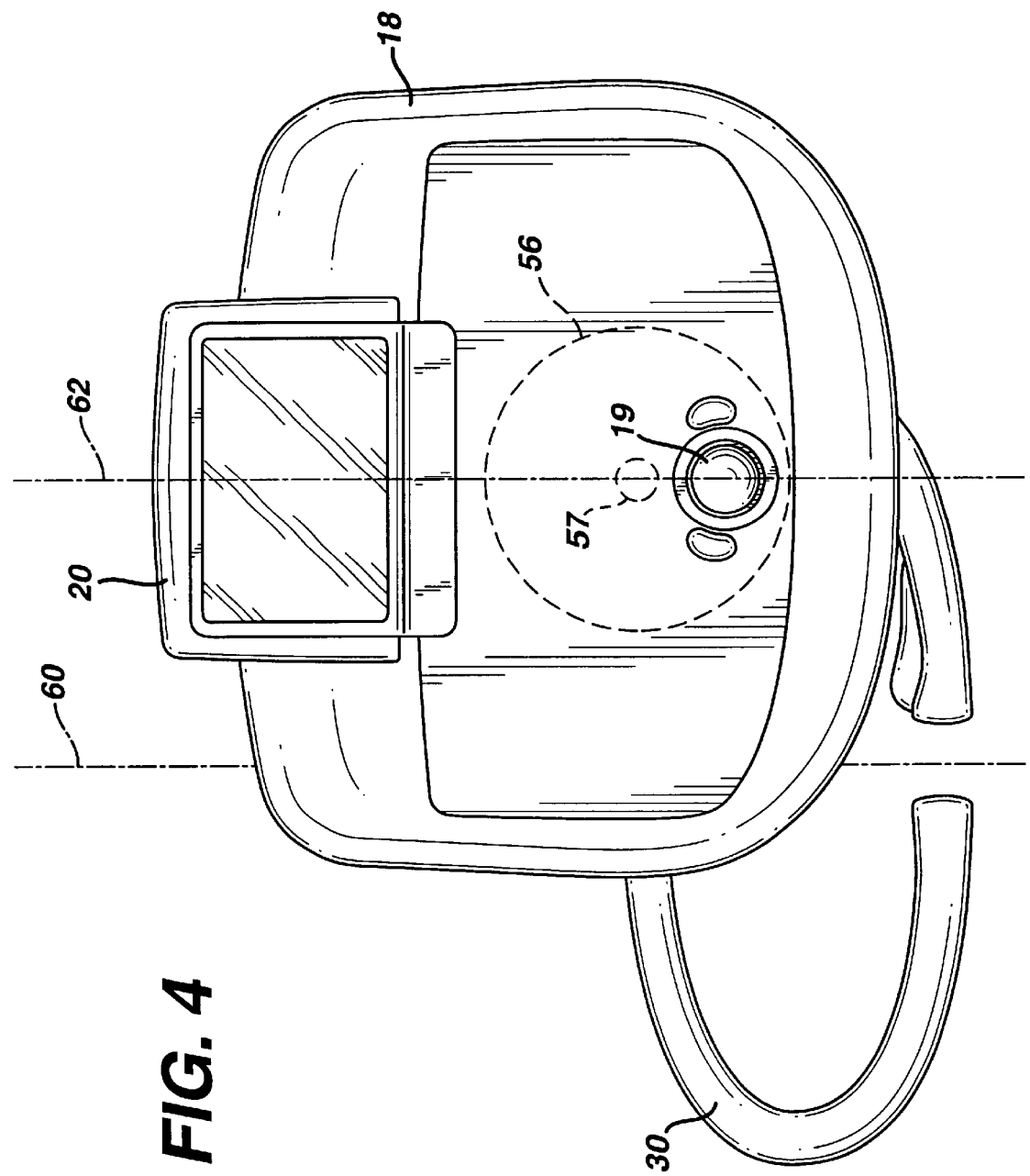

In FIG. 4 the control panel has been moved laterally to the right by moving the lateral carriage 54 in the lateral track 52. The carriage may move smoothly in a frictional engagement with the track, or preferably it may move through a series of detent positions provided by detent recesses and a ball plunger or hinge plate or other detent mechanism. Since the lateral track is linear in this embodiment the control panel will move laterally in a straight line until it reaches the terminus of its range of lateral motion. In a constructed embodiment the control panel was allowed to move laterally ±5 inches from its home position in alignment with center line 60. In its rightmost location shown in FIG. 4 the control panel is centered on a laterally displaced center line 62.

Figure 5:
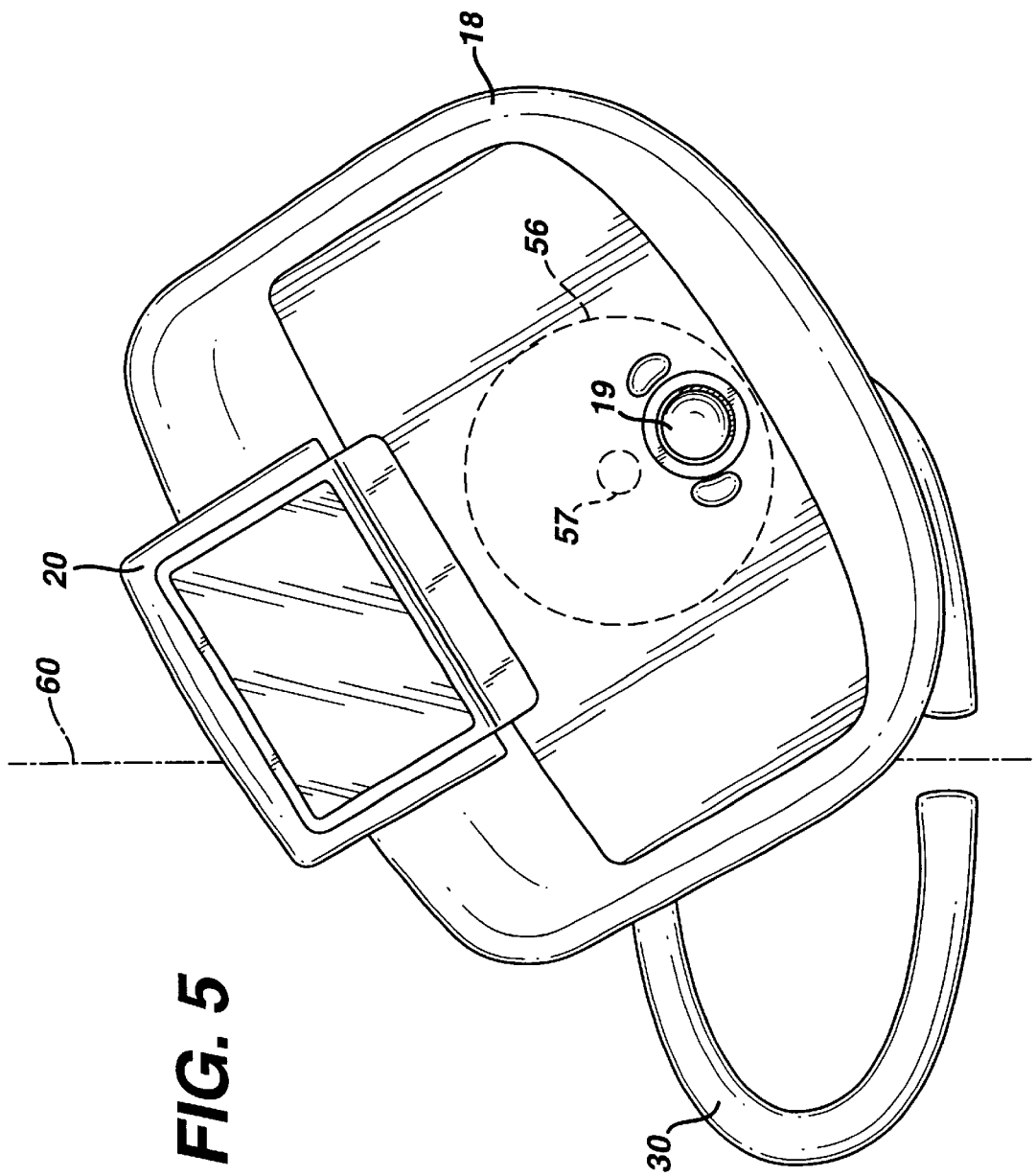

In FIG. 5 the control panel 18 has been moved laterally by operation of the carriage 54 in track 52, and has also been rotated by operation of the swivel plate 57 rotating about its center pivot point 57. This position of the control panel would serve an operator scanning a patient on the right side of the ultrasound system cart and who is also to the right of the cart. The operator does not have to reach or stretch to access the control panel, as the control panel has been moved laterally and swiveled to a comfortable position for the operator.

Figure 6:
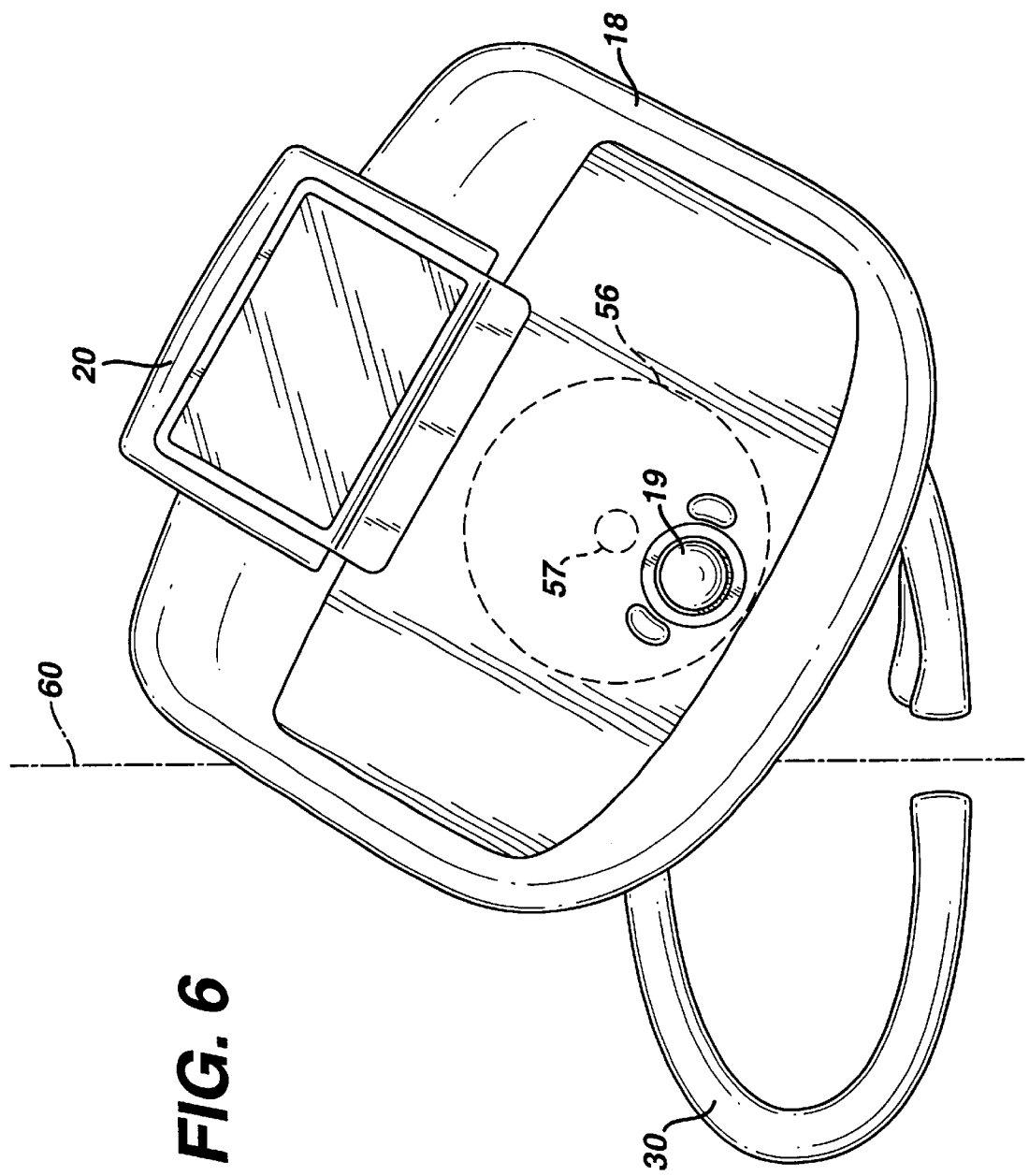

In FIG. 6 the operator has moved the control panel laterally to the right and has swiveled the control panel clockwise about 30°. The combination of the lateral movement and swiveling gives the operator the sense that the control panel has rotated about his operating position or location in the center of the cart. In accordance with one aspect of the present invention, this sense of rotation about the operator position is enhanced by locating the axis of the pivot point 57 of the swivel plate in the front half of the control panel 18. In prior art ultrasound systems the pivot point for the control panel has been located at the back of the control panel or, at best, in the center of the control panel. When the control panel is swiveled about these pivot points, the operator has the impression that the control panel is swinging away from the operator location in front of the control panel, and in many cases this is in fact what is happening. By locating the pivot point for swiveling the control panel in front of the control panel center, the operator can adjust the control panel about his central operating position for the ultrasound system.

Figure 7:
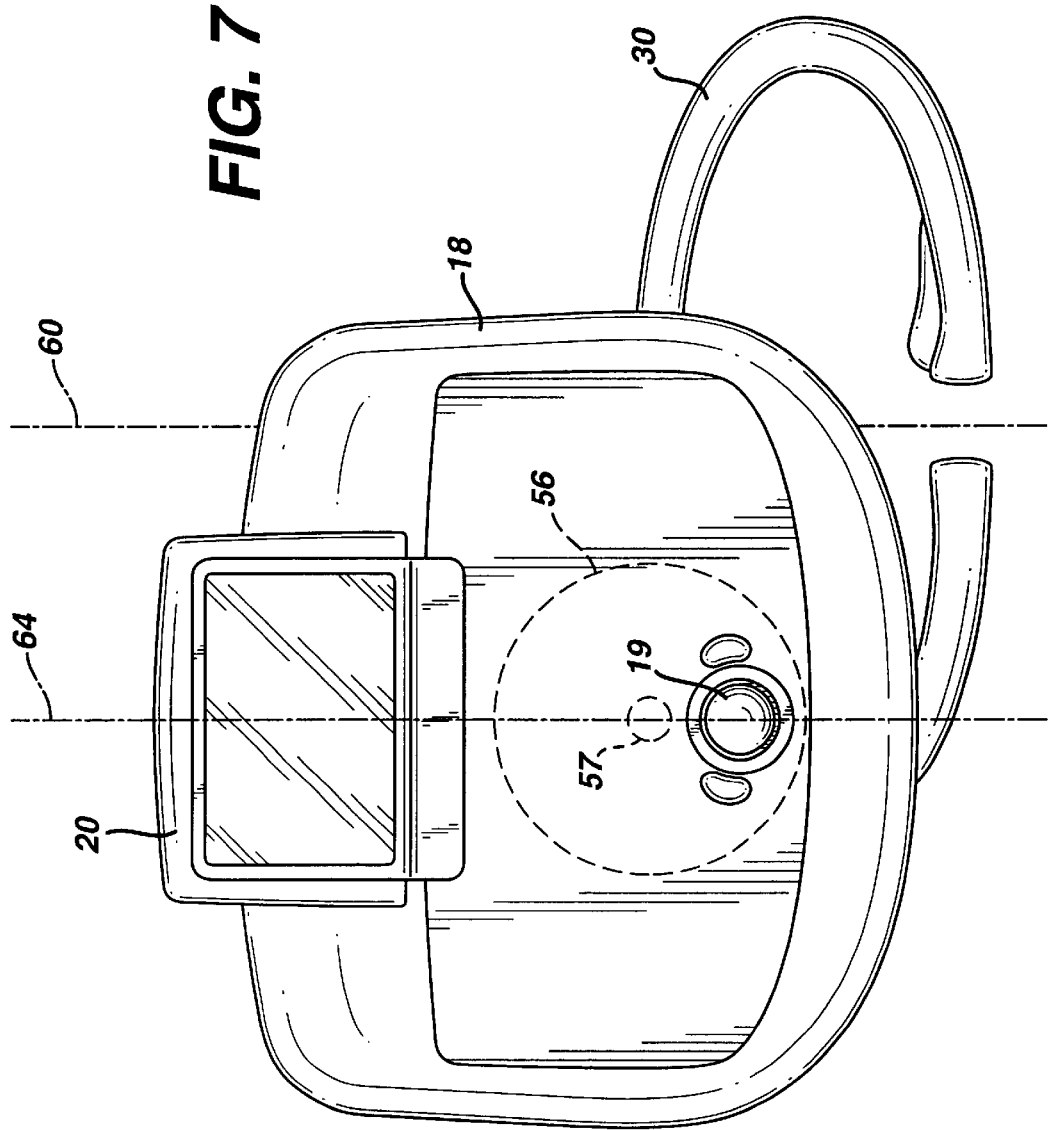
Figure 8:
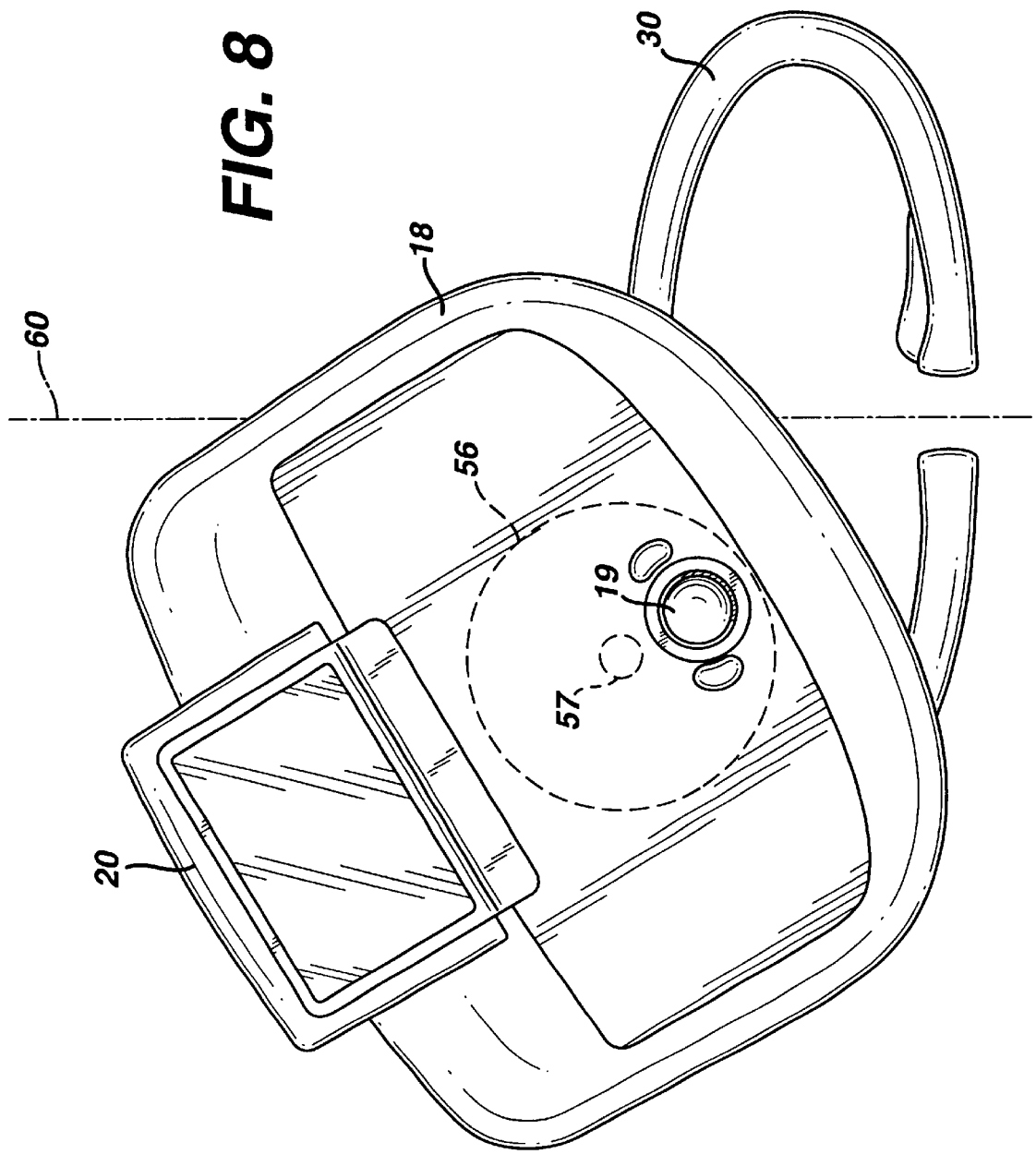

FIG. 7 illustrates the position of the control panel 18 when it has been laterally moved to the left of the center axis 60 and into central alignment with a new center line 64 which has been displaced to the left. As FIG. 8 shows, the control panel 18 can be swiveled about the pivot point 57 in a counter-clockwise direction to effectively rotate the control panel to the left.

Figure 9:
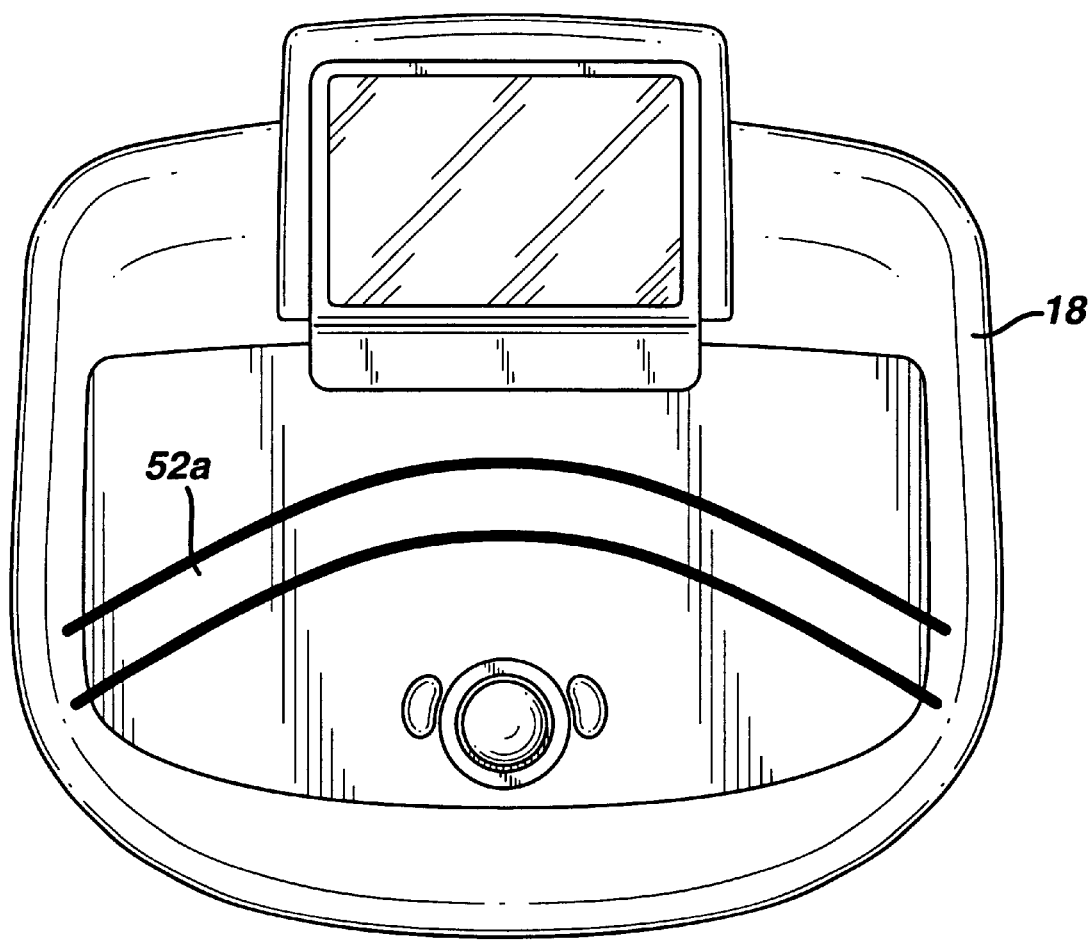
FIG. 9–11 illustrate the control panel articulation provided by a curved path along which the control panel may move in accordance with a second embodiment of the present invention.
Figure 10:
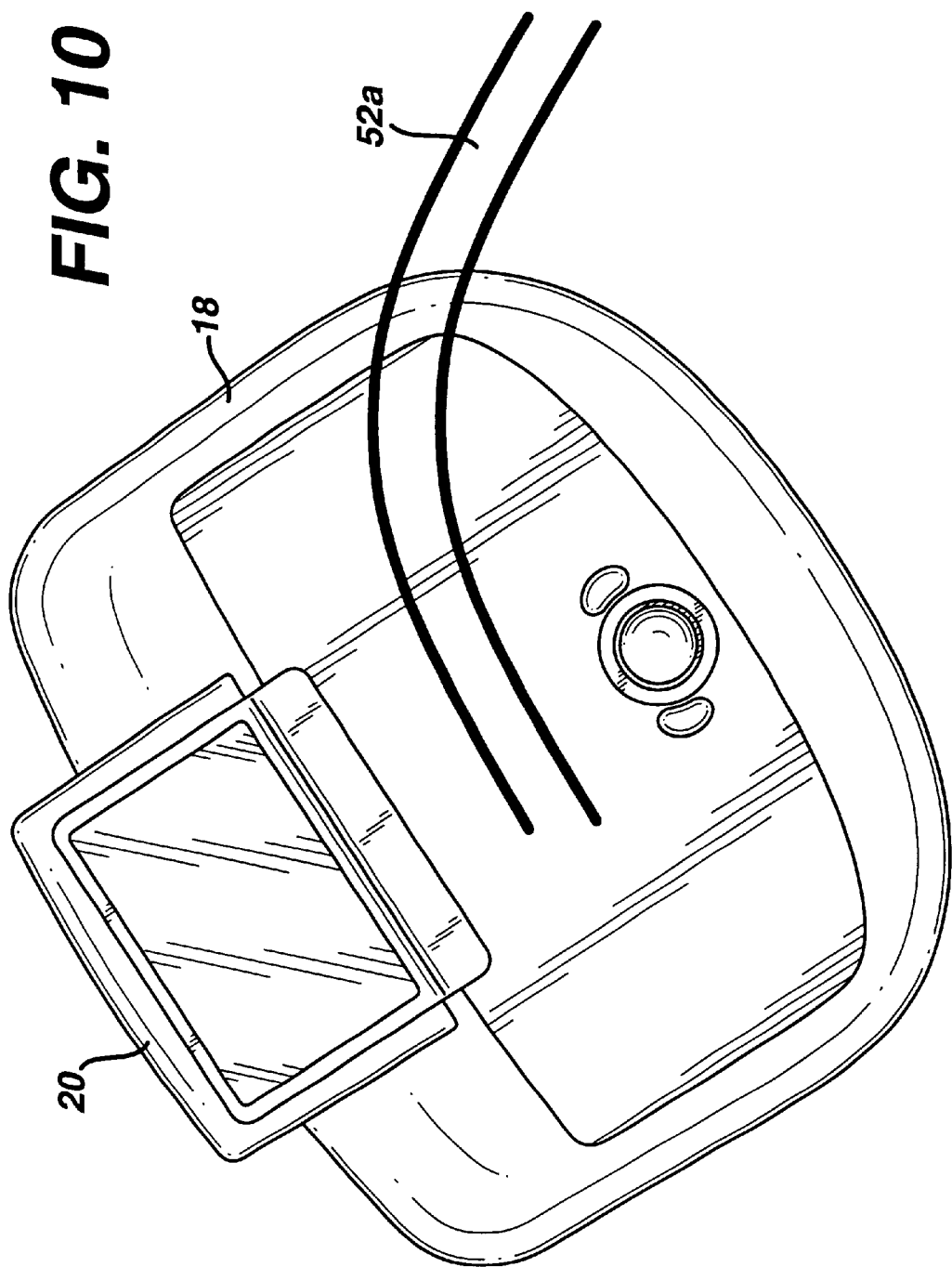
Figure 11:
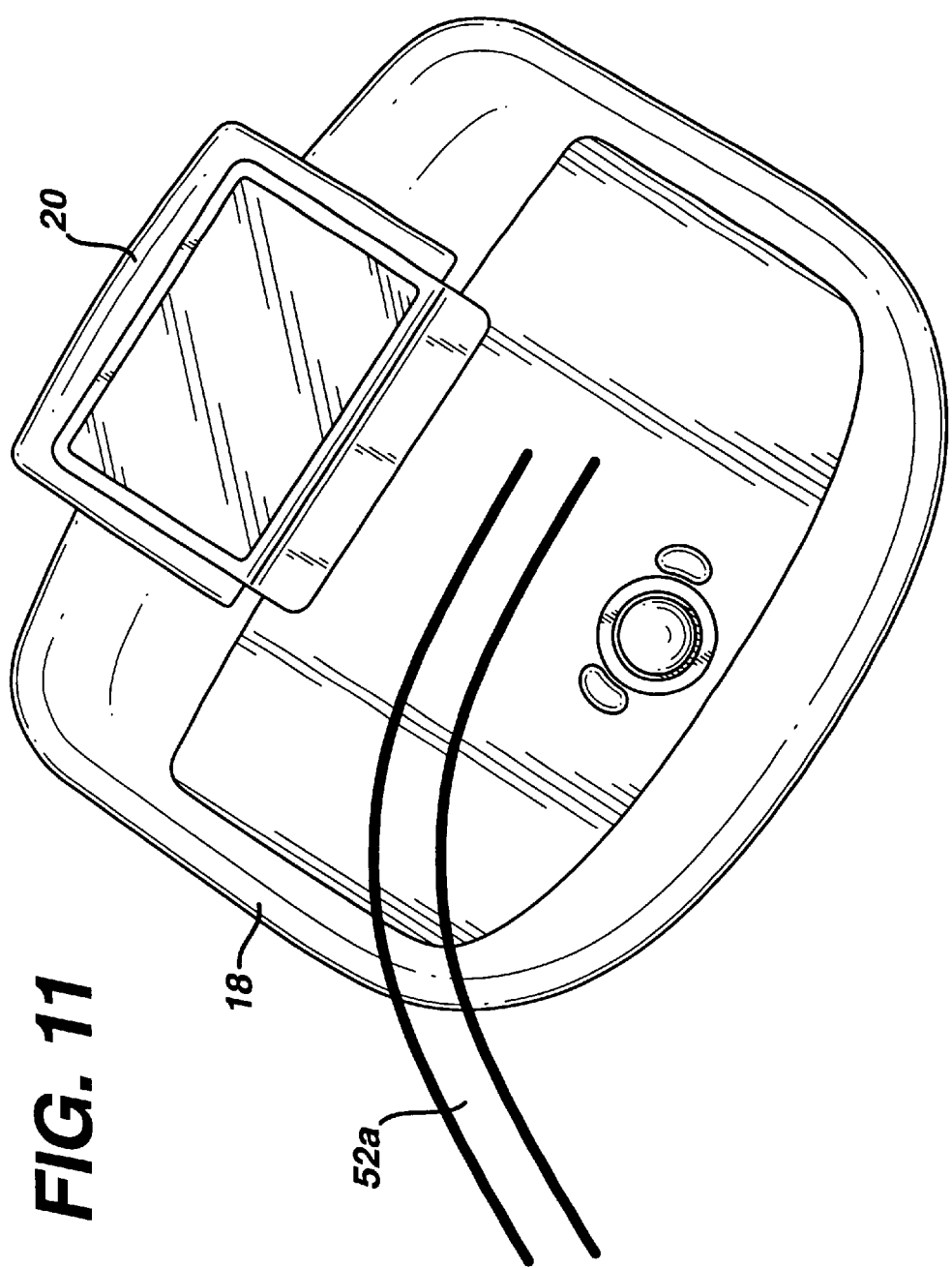

FIG. 9 illustrates a second embodiment of the present invention in which the path of travel of the lateral track 52 is curved about the operator location in front of the control panel 18. The curved track 52a is drawn on top of the control panel for clarity of illustration. The lateral carriage 54 may be matchingly curved to ride in the arcuate track. Alternatively the lateral carriage may comprise track guides or pins which will slide along two arcuate grooves either smoothly or through a series of detent positions. The curved path may also comprise one or more curved rods or bars to which the control panel is movably attached. As FIG. 10 shows, as the control panel moves around the curved path it moves in an arc around the operator location in front of the ultrasound system. FIG. 11 shows the control panel when it is moved to the right along the curved path. When positioned in a desired location along the curved path, the control panel may be swiveled on the swivel plate 56, when used, so as to present a comfortable orientation in which the operator can control the ultrasound system while scanning the patient.

Figure 12:
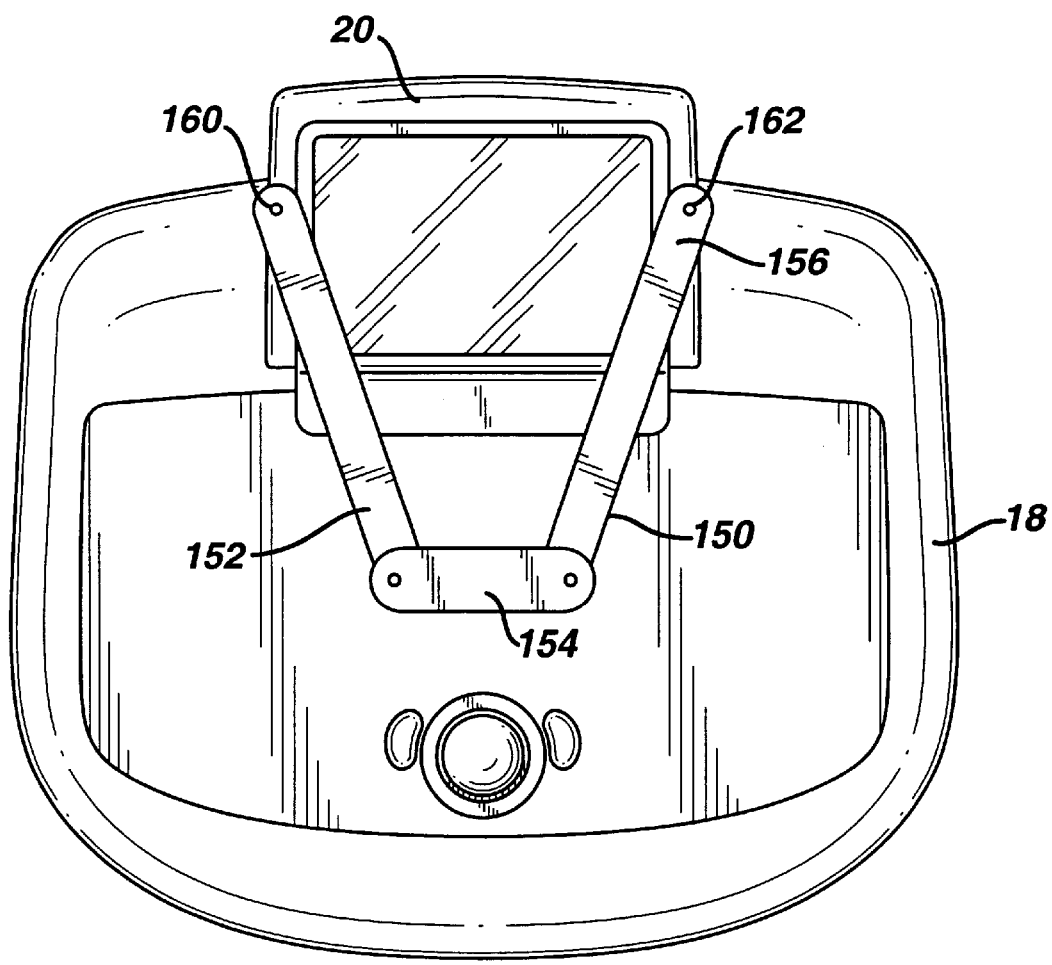
FIGS. 12–14 illustrate the control panel articulation provided by a pivoting articulation assembly of a third embodiment of the present invention.
Figure 13:
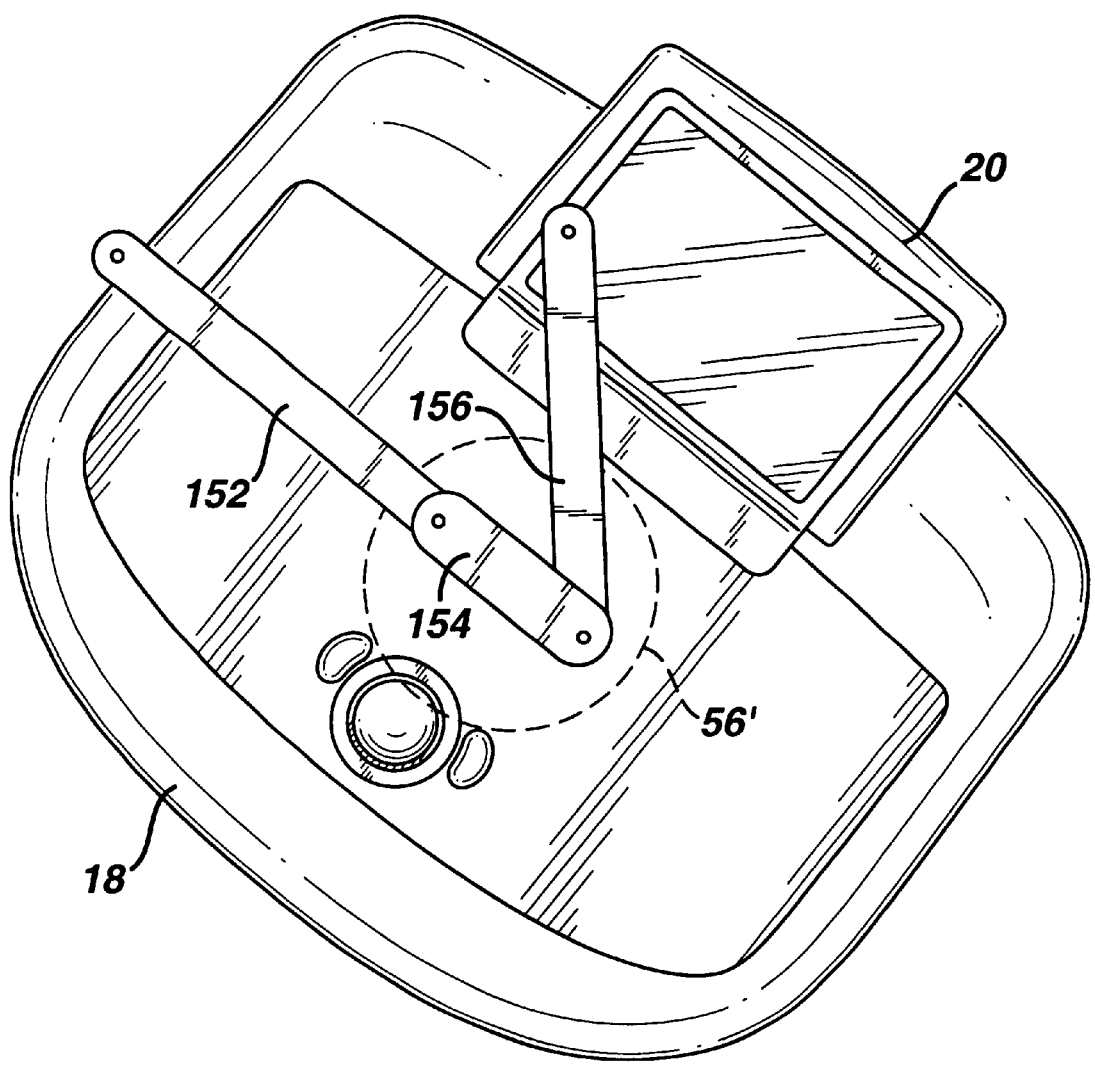
Figure 14:
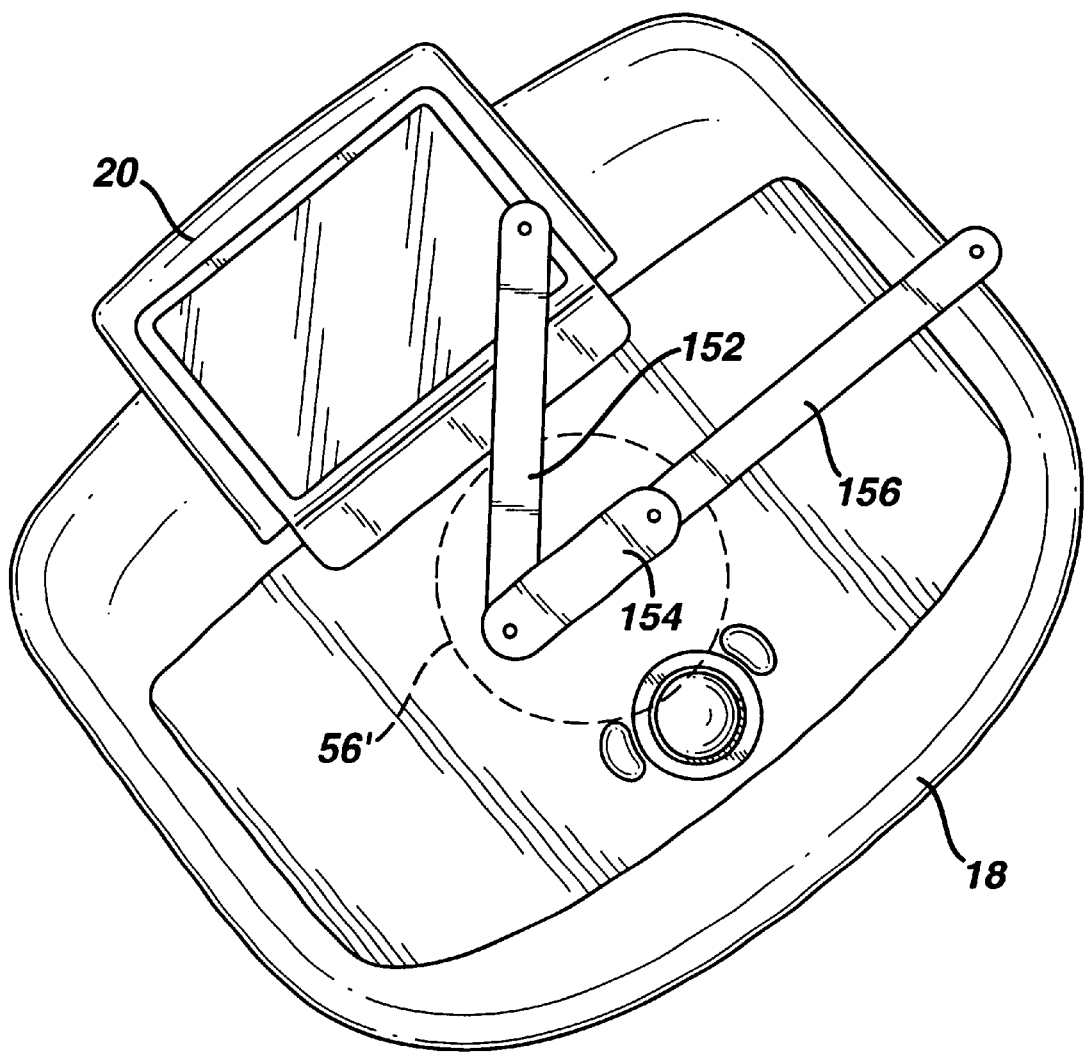

FIG. 12 illustrates a third embodiment of the present invention in which the position of the control panel is adjusted by articulation of a pivoting assembly 150 in place of the carriage and track of the previous embodiments. Again, the assembly 150 is drawn on top of the control panel for clarity of illustration. The illustrated assembly comprises three links which are pivotally connected to each other. Links 152 and 156 are connected to the cart by pivot connections 160 and 162 to the connection block or other point on the cart. The swivel plate, if used, is connected to the central link 154. FIG. 12 illustrates the orientation of the links when the control panel is in its central home position. In FIG. 13 the control panel has been moved to the right. As it moves the links pivot around their four pivot points to assume the position shown in FIG. 13. The motion of the control panel is arcuate, similar to the control panel motion in the second embodiment, and as it moves laterally it also moves forward. FIG. 14 illustrates the position of the control panel when swinging to the left on the pivoting assembly 150. As the phantom outline 56' of the swivel plate shows, the control panel may be swiveled at any location in its arcuate path of travel. As in the previous embodiments, the operator is able to swing the control panel about his central operating position, then swivel the control panel to the most comfortable system operating position.

Modifications to the foregoing embodiments will readily occur to those skilled in the art. The second and third embodiments may be used with or without the swivel capability, for instance. Mechanisms different from those shown above may be employed to give the control panel the described adjustment characteristics.

What is claimed is:

1. A cart-borne ultrasound system including a movable cart having a center line; electronic circuitry located on the cart which processes ultrasound signals for the formation of ultrasound images, and a display coupled to the circuitry for the display of ultrasound images, comprising:

a control panel coupled to the electronic circuitry for user control of the ultrasound system; and a swivel mechanism to which the control panel is connected for rotation, the swivel mechanism providing a position of rotation for the control panel which is forward of the center line of the movable cart and aligned with the forward half of the control panel nearest an operator position.

2. The cart-borne ultrasound system of claim 1, wherein the swivel mechanism includes a plurality of detent positions at which the control panel can be positively located.

3. The cart-borne ultrasound system of claim 1, wherein the swivel mechanism provides a range of rotation of the control panel of at least ±30°.

4. The cart-borne ultrasound system of claim 1, wherein the control panel has a front which is closest to an operator position; and wherein the center of rotation of the control panel is within a few inches of the front of the control panel.

5. A cart-borne ultrasound system including a movable cart having a center line; electronic circuitry located on the cart which processes ultrasound signals for the formation of ultrasound images, and a display coupled to the circuitry for the display of ultrasound images, comprising:

a control panel coupled to the electronic circuitry for user control of the ultrasound system; and a path of travel along which the control panel can be moved relative to the center line of the cart, the path extending laterally with the lateral extensions of the path being more forward located relative to the center line than the center of the path.

6. The cart-borne ultrasound system of claim 5, wherein the path of travel further comprises a track along which the control panel is movable.

7. The cart-borne ultrasound system of claim 6, wherein the path of travel further comprises a trolley coupled to the control panel, wherein the trolley is movable along the track.

8. The cart-borne ultrasound system of claim 5, wherein the path of travel is approximately arcuate, wherein the arcuate path has a center of motion located in front of the forward edge of the control panel.

9. The cart-borne ultrasound system of claim 5, further comprising a swivel mechanism coupled to the control panel to enable the control panel to swivel about a pivot point when positioned on the path of travel.

10. A cart-borne ultrasound system including a movable cart having a forward direction which opposes an operator position; electronic circuitry located on the cart which processes ultrasound signals for the formation of ultrasound images, and a display coupled to the circuitry for the display of ultrasound images, comprising:

a control panel coupled to the electronic circuitry for user control of the ultrasound system; and a linkage coupled to the control panel which moves the control panel laterally to either side of a center position, the linkage moving the control panel in the forward direction as it moves laterally from the center position.

11. The cart-borne ultrasound system of claim 10, wherein the linkage exhibits at least four pivot points.

12. The cart-borne ultrasound system of claim 11, wherein the linkage exhibits a trapezoidal shape when the control panel is located in the center position.

13. The cart-borne ultrasound system of claim 10, further comprising a swivel mechanism coupled to the control panel to enable the control panel to swivel with respect to the linkage.

* * * * *